(12) United States Patent
Alleyne (10) Patent No.: US 8,657,859 B2
(45) Date of Patent: Feb. 25, 2014

(54) IMPLANT FOR PROMOTING STABILITY OF THE CANINE STIFLE JOINT

(75) Inventor: Neville Alleyne, La Jolla, CA (US)

(73) Assignee: Advanced Veterinary Solutions, Del Mar, CA (US)

( * ) Notice: Subject to any disclaimer, the term of this patent is extended or adjusted under 35 U.S.C. 154(b) by 189 days.

(21) Appl. No.: 12/969,442

(22) Filed: Dec. 15, 2010

(65) Prior Publication Data

US 2011/0230919 A1   Sep. 22, 2011

Related U.S. Application Data

(60) Provisional application No. 61/287,062, filed on Dec. 16, 2009.

(51) Int. Cl.
*A61B 17/80* (2006.01)

(52) U.S. Cl.
USPC .......................................... 606/286

(58) Field of Classification Search
USPC .................. 606/248–249, 280, 286, 289–291
See application file for complete search history.

(56) References Cited

U.S. PATENT DOCUMENTS

| | | | |
|---|---|---|---|
| 4,502,161 A * | 3/1985 | Wall ........................... | 623/14.12 |
| 5,290,271 A | 3/1994 | Jernberg | |
| 5,344,452 A | 9/1994 | Lemperle | |
| 6,107,466 A | 8/2000 | Hasan et al. | |
| 6,284,872 B1 | 9/2001 | Celeste et al. | |
| 6,335,028 B1 | 1/2002 | Vogel et al. | |
| 6,432,437 B1 | 8/2002 | Hubbard | |
| 6,468,274 B1 | 10/2002 | Alleyne et al. | |
| 6,579,290 B1 * | 6/2003 | Hardcastle et al. .......... | 606/247 |
| 6,652,883 B2 | 11/2003 | Goupil et al. | |
| 6,730,091 B1 * | 5/2004 | Pfefferle et al. ................ | 606/70 |
| 6,887,272 B2 * | 5/2005 | Shinomiya et al. ........ | 623/17.11 |
| 2003/0211083 A1 | 11/2003 | Vogel et al. | |
| 2003/0236573 A1 | 12/2003 | Evans et al. | |
| 2004/0054414 A1 | 3/2004 | Trieu et al. | |
| 2004/0210226 A1 * | 10/2004 | Trieu .............................. | 606/72 |
| 2006/0229621 A1 * | 10/2006 | Cadmus .......................... | 606/69 |
| 2007/0162019 A1 * | 7/2007 | Burns et al. .................... | 606/69 |
| 2007/0173936 A1 * | 7/2007 | Hester et al. ............... | 623/17.11 |
| 2009/0318976 A1 * | 12/2009 | Gabriel et al. ................ | 606/283 |

FOREIGN PATENT DOCUMENTS

| | | |
|---|---|---|
| EP | 1410810 | 4/2004 |
| WO | WO 0044394 | 8/2000 |

OTHER PUBLICATIONS

Arnoczky, et al., "The Over-the-Top Procedure: A Technique for Anterior Cruciate Ligament Substitution in the Dog" *J. American Animal Hospital Association* (1979) 15(3): 252, 283-290.

Arshady, Reza, "Preparation of biodegradable microspheres and microcapsules: 2. Polyactides and related polyesters" *J. Controlled Release* (1991) 17: 1-22.

(Continued)

*Primary Examiner* — Nicholas Woodall (74) *Attorney, Agent, or Firm* — Knobbe Martens Olson & Bear LLP (57) ABSTRACT

Methods and devices for stabilizing ligaments of the canine stifle joint are described. In one embodiment, a device for promoting stability of the stifle joint in a canine subject is provided. The device includes a buttress comprising an intra-articular portion and an extra-articular portion, where the intra-articular portion of the buttress is fenestrated. The device also includes a keel coupled to the extra-articular portion of the buttress, and one or more fasteners configured to attach the device to the stifle joint.

20 Claims, 5 Drawing Sheets

(56) References Cited

OTHER PUBLICATIONS

DeAngelis, et al., "A Lateral Retinacular Imbrication Technique for the Surgical Correction of Anterior Cruciate Ligament Rupture in the Dog" *J.A.V.M.A.* (1970) 157(1): 79-84.

Dickinson, et al., "Repair of Ruptured Anterior Cruciate Ligament in the Dog: Experience of 101 Cases, Using a Modified Fascia Strip Technique" *J.A.V.M.A.* (1977) 170(8): 827-830.

Dueland, R., "A Recent Technique for Reconstruction of the Anterior Cruciate Ligament" *J. American Animal Hospital Association* (1966) 2: 1-5.

Flo, Gretchen L., "Modification of the Lateral Retinacular Imbrication Technique for Stabilizing Cruciate Ligament Injuries" *J. American Animal Hospital Association* (1975) 11(5): 570-576.

Holland, et al., "Polymers for Biodegradable Medial Devices. 1. The Potential of Polyesters as Controlled Macromolecular Release Systems" *J. Controlled Release* (1986) 4: 155-180.

Miller, et al., "Collagen: An Overview" *Methods in Enzymology* (1982) 82: 3-32.

Pearson, et al., "Lembert Suture Technique to Surgically Correct Ruptured Cruciate Ligaments" *J. American Animal Hospital Association* (1971) 7(1): 1-13.

Pitt, C. G., "The controlled parenteral delivery of polypeptides and proteins" *Intl. J. Pharma.* (1990) 59: 173-196.

* cited by examiner

IMPLANT FOR PROMOTING STABILITY OF THE CANINE STIFLE JOINT

CROSS-REFERENCE TO RELATED APPLICATIONS

This application claims priority to U.S. Provisional Application No. 61/287,062, entitled "Implant for Promoting Stability of the Canine Stifle Joint," filed on Dec. 16, 2009, which is hereby incorporated by reference in its entirety.

FIELD OF THE INVENTION

The present invention relates to the field of veterinary medicine. In particular, methods and devices are described for stabilizing the canine stifle joint.

BACKGROUND

Figure 1:
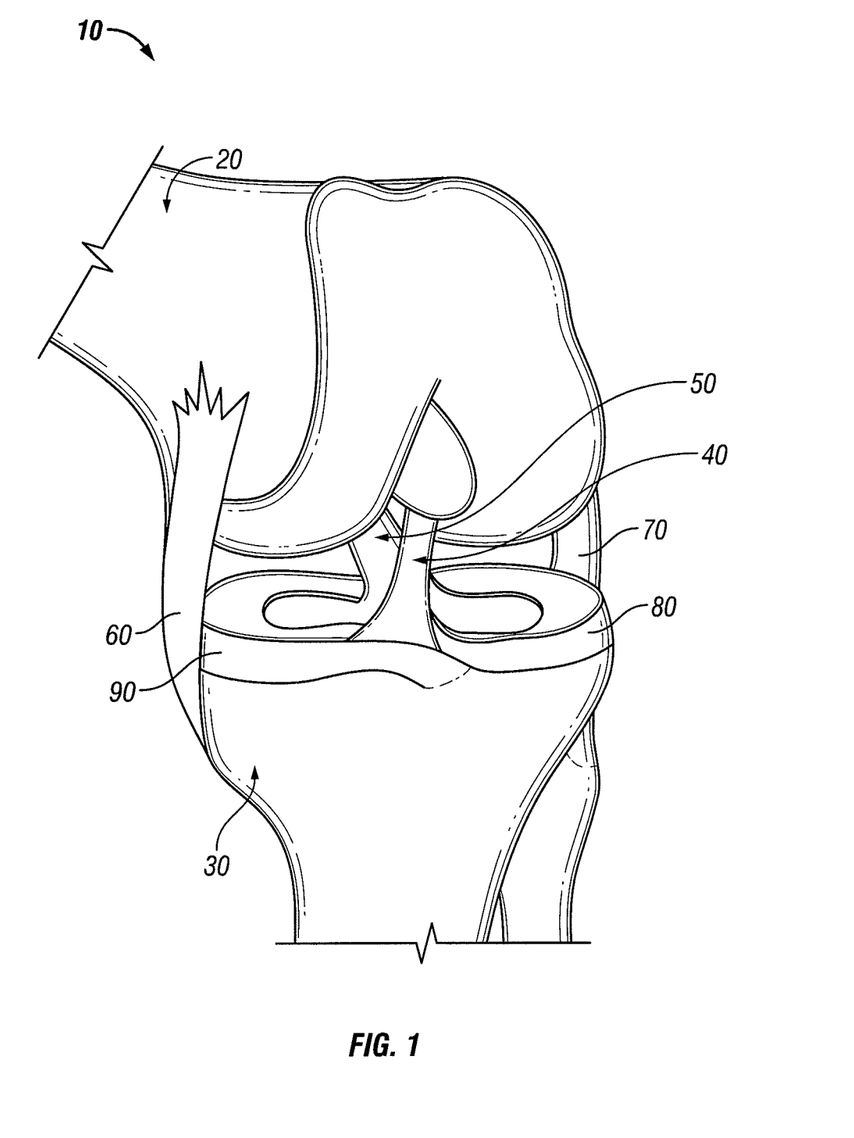
FIG. 1 illustrates a schematic of a canine stifle joint.
Figure 3A:
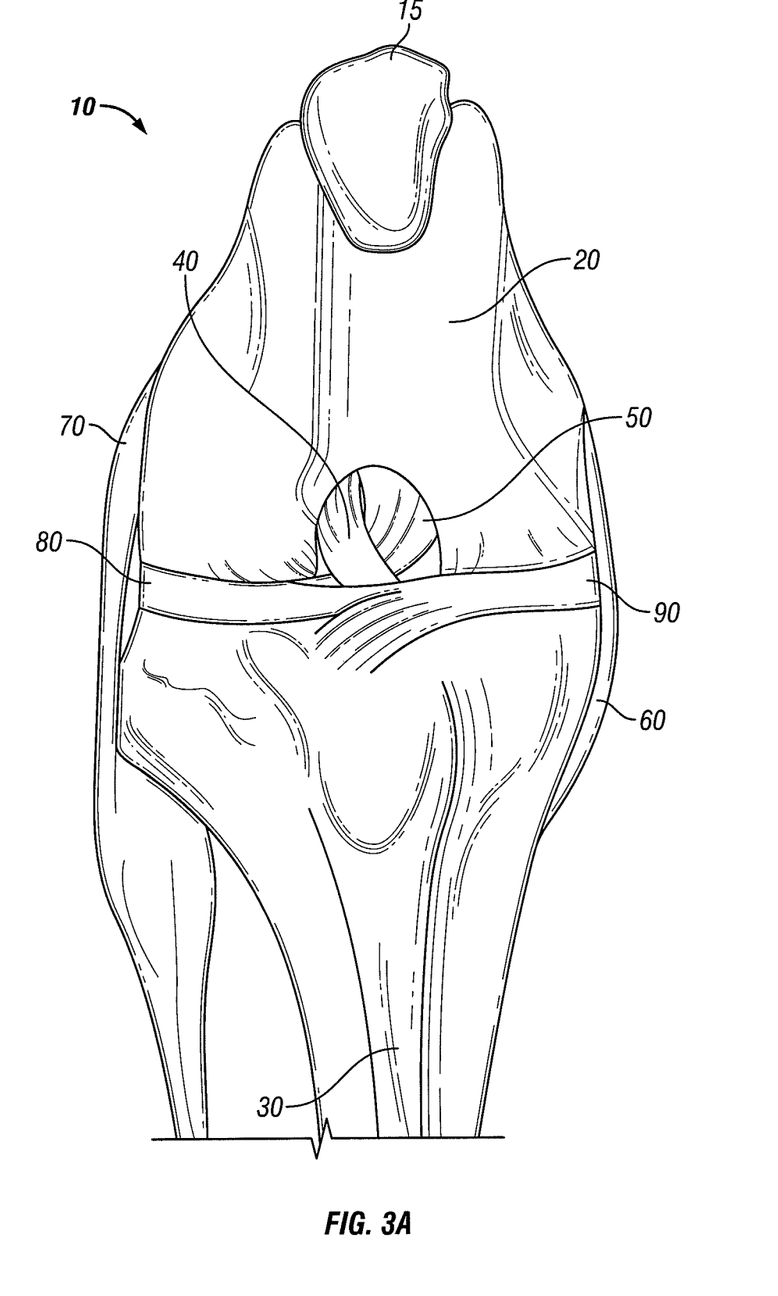
FIG. 3A illustrates a schematic of a canine stifle joint prior to delivery of the device of FIG. 2A.

One of the most common orthopedic problems in dogs is injury to the stifle (hind knee) joint, and in particular, the cranial cruciate ligament of the stifle joint. Referring to FIGS. 1 and 3A, the canine stifle joint 10 is a hinge joint and includes the femur 20, the patella 15 (illustrated in FIG. 3A), and the tibia 30. Holding these bones together are the cranial cruciate ligament 40, the caudal cruciate ligament 50, the medial collateral ligament 60, the lateral collateral ligament 70, and the patellar tendon (not illustrated). The stifle joint 10 also includes the lateral meniscus 80 and the medial meniscus 90. The joint is bathed in synovial fluid which is contained in the joint capsule. The cruciate ligaments reside deep within the knee joint, and the cranial cruciate ligament is much more commonly injured than the other ligaments of the canine stifle. Dogs with injuries will suffer lameness, pain, and develop associated disorders.

The causes of cruciate ligament injury can be complex. In some cases, injury can be through sudden rotation of the stifle. However, other cases can develop through no apparent trauma. It is believed that the slope of the tibial plateau along with the joint forces causes the femur to translate upon the tibial plateau. This results in a classic condition known as cranial tibial thrust. This forward movement puts the cranial cruciate ligament under significant stress and can result in attenuation or rupture of the cranial cruciate ligament.

When either the caudal or cruciate ligament does attenuate or is ruptured, it can lead to joint instability, and if left untreated it will result in progressive degenerative changes within the joint. In some cases, ligament rupture can lead to articular wear of the joint secondary to the femoral condyle engaging upon the tibial plateau and causing articular "scuffing." These forces continue to cause degeneration and weakening of secondary restraints such as the medial and lateral meniscus. The instability can lead to tears of the medial and lateral meniscus, which can cause further instability, pain, and lameness. In addition, as joint changes develop, the cruciate ligaments undergo alteration in their microstructure. Collagen fibrin become hyalinized, and the tensile strength of the ligament is reduced, making the ligament more susceptible to damage from minimal trauma.

Currently, a number of extracapsular and intra-articular surgical techniques can be used to treat stifle ligament injuries. Extracapsular techniques include imbrication of the lateral joint tissues with one or more sutures. The sutures are placed in a general anteroposterior orientation to eliminate the cranial displacement of the tibia on the femur (cranial drawer). By placing the imbrication suture or sutures on the lateral aspect of the joint, the tendency for inward rotation of the tibia due to cranial cruciate ligament insufficiency is also prevented. However, current extracapsular imbrication procedures are limited in the ability to provide sufficient stability to the cranial cruciate deficient stifle joint, and are also met with limited success in larger dogs.

Intra-articular repairs include reconstruction or replacement of the cruciate ligaments with either an autogenous or a synthetic graft. Replacement techniques involve the re-creation of an intra-articular structure in the approximate spatial orientation of the normal cranial cruciate ligament. The graft is usually passed through drill holes in the femur and tibia and, depending on the technique used, is attached to the soft tissues of the femur or tibia. Not only are such techniques invasive, but the ideal transplant material has not yet been found. Ideally, a material would possess great strength, some elasticity, and tolerate wear and tear in the joint for years, and be non-irritant.

Another intra-articular technique includes tibial plateau leveling osteotomy (TPLO) where the tibia is cut and the slope between the femur and tibia reduced. A tibial tuberosity advancement (TTA) procedure is yet another intra-articular procedure. These procedures can result in surgical complications, however, such as infection, bleeding, nonunion, loosening or fracture of hardware, arterial and nerve injury, severe limitation in joint movement, chronic pain, and continued instability.

Injury to the cranial cruciate ligament of the canine stifle joint is a particularly acute problem. Every year in the United States approximately 1.4 million dogs have cranial cruciate ligament deficiencies requiring surgery. Pet owners spend approximately $1.5 billion dollars on repairs to the cranial cruciate ligament as of 2006. The current surgical procedures to repair the ligament, including TPLO and TTA, can result in significant intra-articular damage and create fibrosis to the articular surface. In the best case scenario, the change in the inclination of the tibial tuberosity and this fibrosis results in a less painful and more stable knee, allowing the dog to recover from the surgical insult and continue with normal activities. However, anywhere from 50% to 75% of the dogs who tear their cranial cruciate ligament will also have a contralateral cranial cruciate ligament injury within two years.

Thus, the current technology from a standpoint of surgical intervention requires significant intra-articular and accurate bony osteotomies to be performed in order to achieve a successful outcome. Given the high number of canine ligament injuries and the complications associated with current surgical procedures, there is a need for a minimally invasive and less destructive intra-articular or extra-articular surgical procedure to treat injured ligaments of the canine stifle joint.

SUMMARY

Methods and devices for stabilizing ligaments of the canine stifle joint are described herein. In one embodiment, a device for promoting stability of the stifle joint in a canine subject is provided. The device includes a buttress comprising an intra-articular portion and an extra-articular portion, where the intra-articular portion of the buttress is fenestrated. The device also includes a keel coupled to the extra-articular portion of the buttress, and one or more fasteners configured to attach the device to the stifle joint.

A biocompatible device to prevent instability in the canine stifle joint is provided in another embodiment. The device includes an intra-articular, fenestrated buttress with a plate that is attachable to the femur or tibia.

In yet another embodiment, a method for stabilizing the stifle joint in a canine subject is provided. The method includes identifying a subject in need of stifle joint stabilization, and delivering an implantable device to the joint. The implantable device includes a cylindrical intra-articular buttress with a plate that is attachable to the femur or the tibia.

DETAILED DESCRIPTION

Devices and methods are provided for stabilizing ligaments of the canine stifle joint, and in particular the cranial cruciate ligament. In some implementations, devices for stabilizing the joint include a buttress having an intra-articular portion and an extra-articular portion. The device also includes a keel coupled to the extra-articular portion of the buttress and configured to attach the device to the stifle joint.

Figures 2A, 2B:
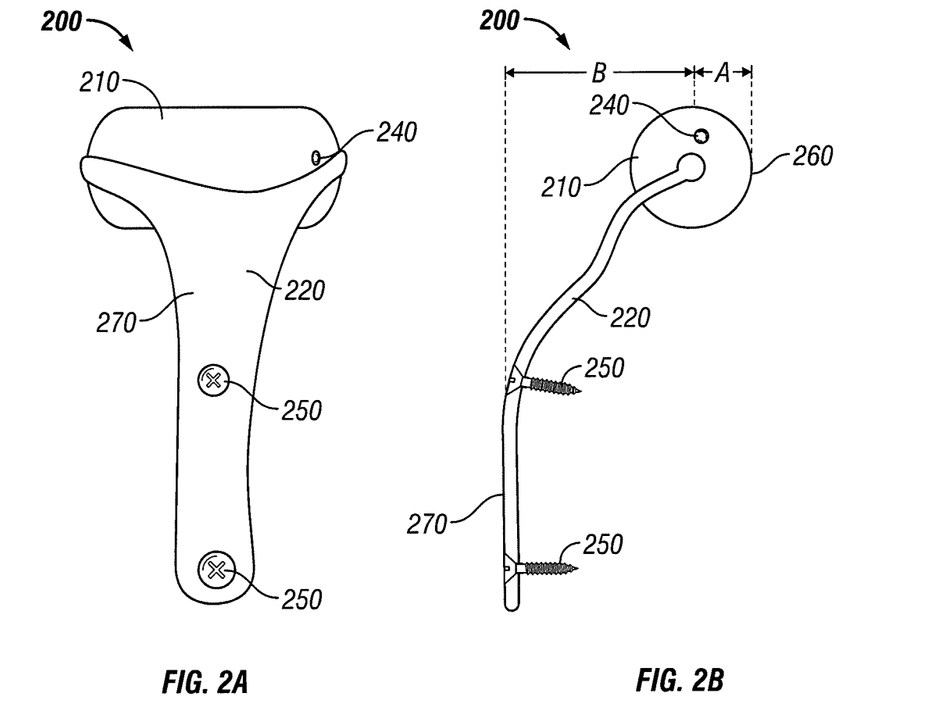
FIG. 2A illustrates a first perspective view of one embodiment of a device for stabilizing the canine stifle joint.
FIG. 2B illustrates a second perspective view of the device of FIG. 2A.

Referring to FIGS. 2A and 2B, a biocompatible, implantable device 200 is provided to stabilize the canine stifle joint 10 illustrated in FIG. 1. The device 200 can function as an intra-articular and extra-articular block for a stifle joint with a deficient cranial cruciate ligament. Thus, in some implementations, a first portion of the device 200 is intra-articular, or configured to be situated within the joint 10, while a second portion of the device 200 is extra-articular, or configured to be situated outside the joint 10.

The device 200 includes a buttress 210 coupled to a keel or plate 220. In some implementations, an extra-articular portion of the device 200 includes the keel 220 and a first portion of the buttress 210, and an intra-articular portion of the device 200 includes a second portion of the buttress 210.

In one embodiment illustrated in FIG. 2B, the buttress 210 is generally cylindrical in shape. In other embodiments, the buttress 210 is a shape that facilities delivery of a portion of the buttress 210 within the stifle joint 10. For example, in an embodiment illustrated in FIG. 2C, the buttress 210 includes one or more tapered portions 230 located in a portion A of the buttress 210. Portion A of the buttress 210 may be intra-articular, while a portion B of the buttress 210 may be extra-articular. The one or more tapered portions 230 can be located on the superior aspect of the buttress 210, the inferior aspect of the buttress 210, or both. A buttress 210 with tapered portions 230 can be used advantageously in a stifle joint with a gross instability. In some embodiments, the one or more tapered portions 230 aid in anchoring the buttress 210 within the stifle joint 10.

In some implementations, all or a part of the buttress 210 comprises a material with openings or fenestrations in the surface of the material. For example, the buttress 210 can include openings in the intra-articular surfaces of the buttress 210, such as those areas of the buttress 210 configured to be delivered within the stifle joint 10. Thus, intra-articular portions of the buttress 210 can include fenestrations while extra-articular portions of the buttress 210 may not include fenestrations. In the embodiments illustrated in FIGS. 2B and 2C, for example, surfaces 260 in the intra-articular portion A can include openings through which a material can be expressed into the stifle joint 10 and/or through which tissue growth can occur. In some implementations, both the intra-articular portion A and the extra-articular portion B of the buttress 210 include openings.

Figure 2C:
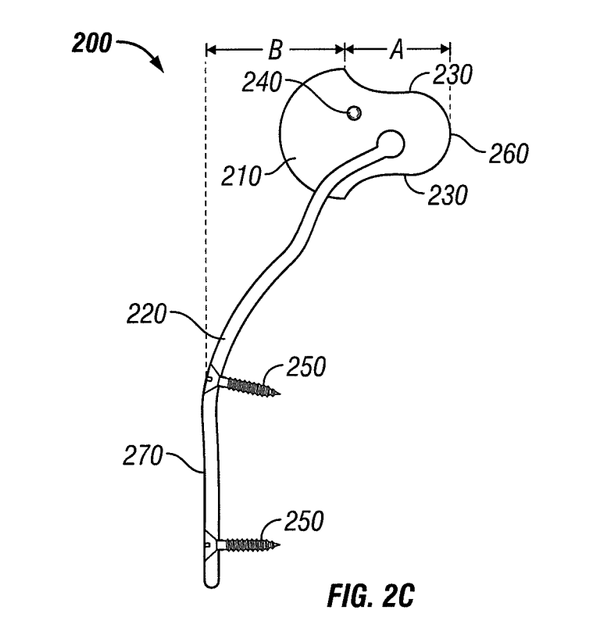
FIG. 2C illustrates a perspective view of another embodiment of a device for stabilizing the canine stifle joint.

All or part of the buttress 210 can be hollow. For example, intra-articular portion A of the buttress 210 can be hollow, while extra-articular portion B of the buttress 210 may be solid. The buttress 210 includes a port 240 in some embodiments. Various biocompatible materials can be injected into the hollow space of buttress 210 through the port 240. For example, collagen mixed with PMMA microspheres can be introduced into the buttress 210 through the port 240 before delivering the device 200 to the stifle joint 10. After the device 200 is delivered to the stifle joint 10, the collagen and/or PMMA microspheres can be expressed through openings in the buttress 210 and enter the stifle joint 10 or areas surrounding the stifle joint 10.

The buttress 210 can comprise a non-biodegradable material such as, nylon, Dacron and Teflon. More examples of non-biodegradable materials that can be used with embodiments of devices described herein include polyamides, polyolefins (e.g. polypropylene and polyethylene), polyurethanes, polyester/polyether block copolymers, polyesters (e.g. PET, polybutyleneterephthalate, and polyhexyleneterephthalate), polyester cloth (e.g. DACRON), polyester sheeting (e.g. MYLAR; DuPont), nylon meshes, DACRON meshes (e.g. MERSILENE; Ethicon, Inc.), acrylic cloth (ORLON; DuPont), polyvinyl sponge (IVALON), polyvinyl cloth (VINYON-N), polypropylene mesh (MARLEX or BARD; CR Bard, Inc.; and PROLENE; Ethicon, Inc.), silicones, fluoropolymers (e.g. fluorinated ethylene propylene), and polytetrafluoroethylene (PTFE; e.g. TEFLON mesh and cloth; DuPont).

The buttress 210 and the keel 220 can be mechanically coupled in a number of ways. In one embodiment, the buttress 210 and the keel 220 are fixedly coupled such that there is substantially no movement between the buttress 210 and the keel 220 when the device 200 is implanted.

The keel 220 can include fasteners for attaching the device 200 to the stifle joint 10 or to areas surrounding the stifle joint 10. For example, the device 200 can include one or more screws 250 to fasten the keel 220 to the stifle joint 10. In one embodiment, the device 200 includes eccentric screw placement to prevent pullout of the device 200 after delivery to the stifle joint 10. In another embodiment, the keel 220 includes a self-contained locking mechanism for the head of screw 250.

Figure 3B:
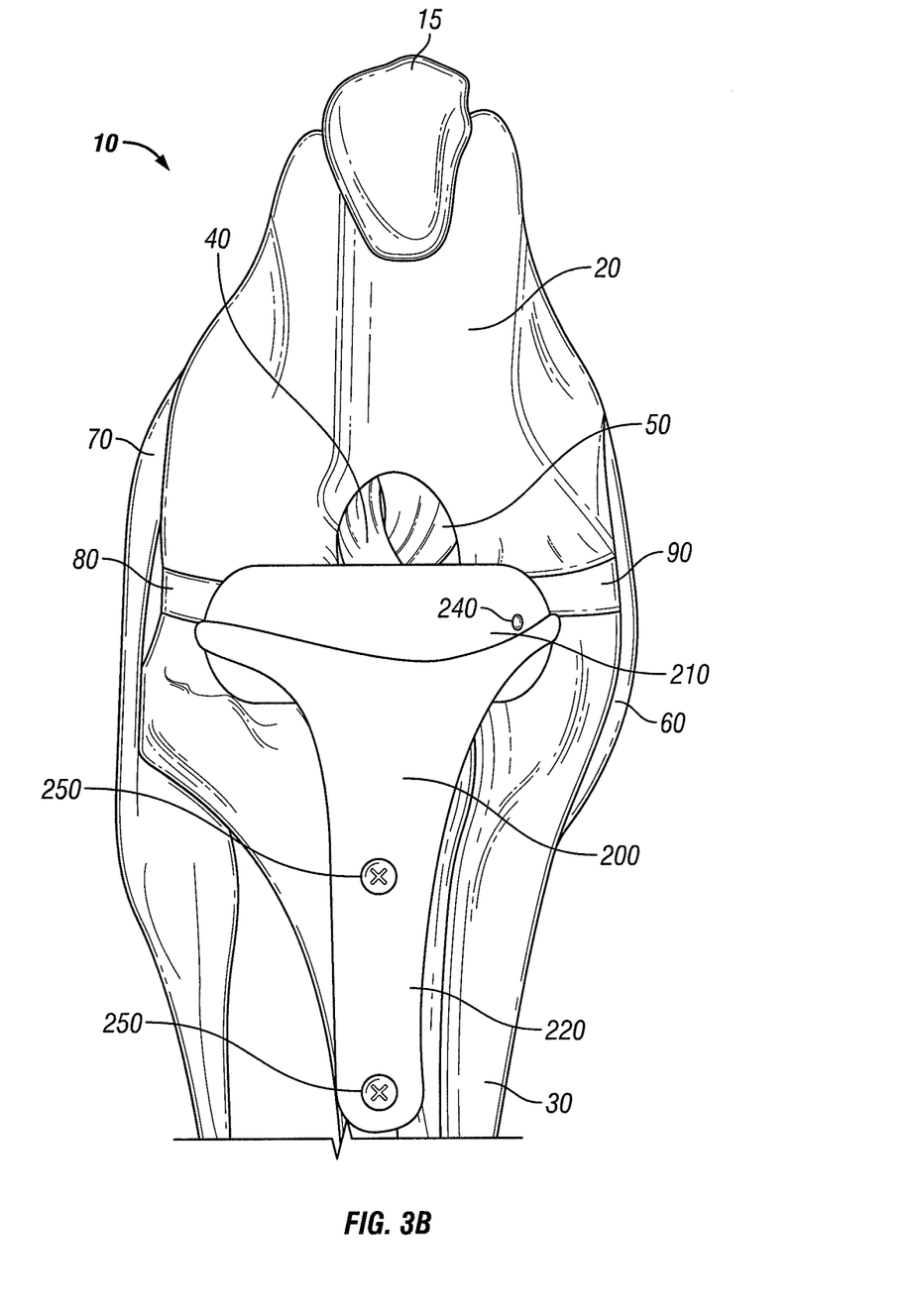
FIG. 3B illustrates a schematic of the stifle joint of FIG. 3A after delivery of the device of FIG. 2A according to one method.
Figure 3C:
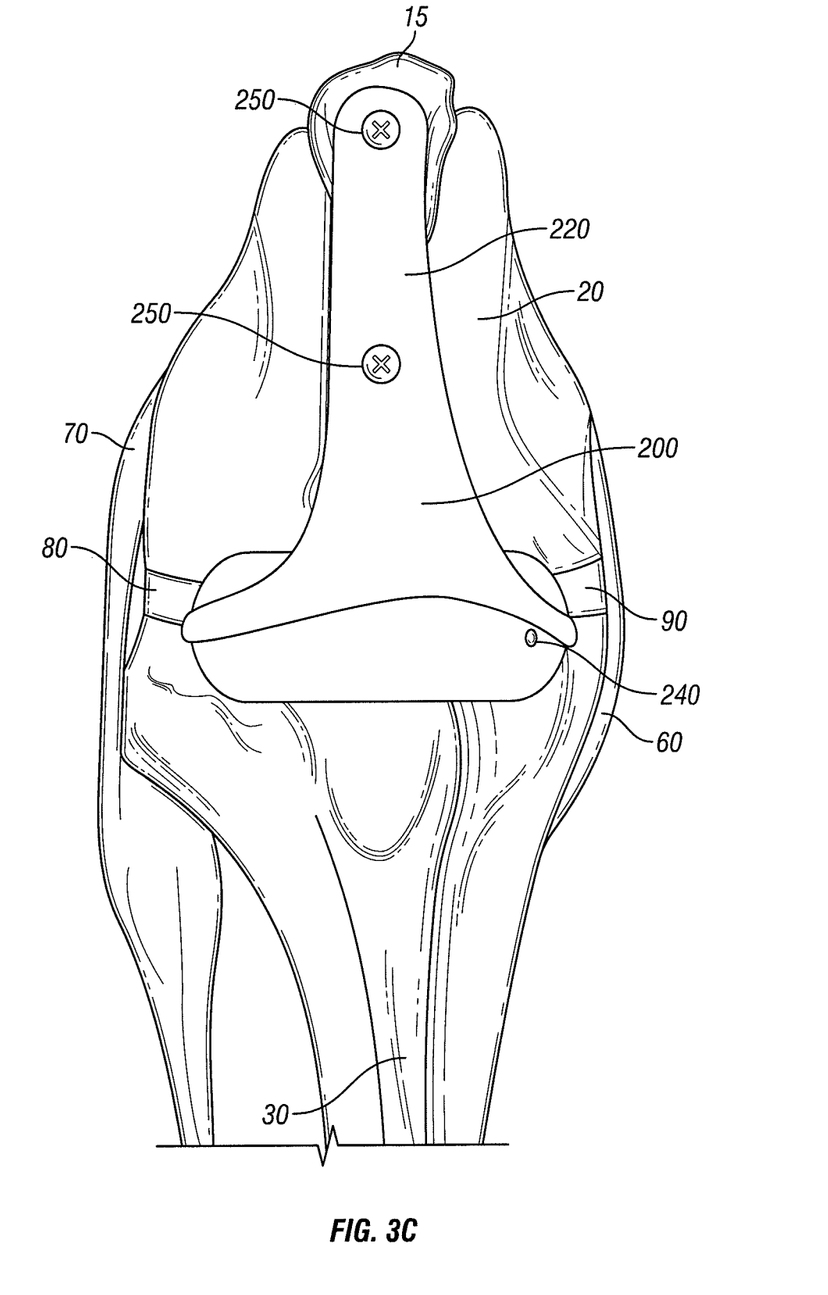
FIG. 3C illustrates a schematic of the stifle joint of FIG. 3A after delivery of the device of FIG. 2A according to another method.

Methods of stabilizing the stifle joint 10 using the device 200 will now be described with reference to FIGS. 3A-3C. FIG. 3A illustrates a stifle joint 10 before an embodiment of the device 200 is delivered to stabilize the joint. FIGS. 3B and 3C illustrate methods of delivering the device 200 to the stifle joint 10. As described above with reference to FIGS. 2A-2C, a portion of the buttress 210 can be delivered inside the stifle joint 10. As illustrated in FIG. 3B, the device 200 can be anchored into the tibia 30 from an intra-articular or extra-articular approach. In particular, the keel 220 of the device 200 can be anchored to the tibia 30 using fasteners such as, but not limited to, screws 250. As shown in FIG. 3C, the device 200 can also be anchored into the femur 20 from an intra-articular or extra-articular approach.

The keel 220 can be formed of any suitable material, including but not limited to a malleable metal. In one embodiment, the keel 220 is anchored into the anterior portion of the tibia 30 without removing the patella tendon (not shown) or any part of the lateral meniscus 80 or the medial meniscus 90. The keel 220 may be formed of a smooth-surfaced metal and shaped to be flush with the femur 20 or the tibia 30 upon delivery to the stifle joint 10.

Additionally, all or a portion of the keel 220 can be porous coated. For example, the ventral surface 270 of the keel 220 can be coated with hydroxyapatite or other material. All or a combination of these features can allow bony ingrowth to take place in and around the keel 220, providing further stability to the stifle joint 10.

The buttress 210 and the keel 220 can be formed of any suitable material. For example, components of the device 200 can be formed of bone, cortical material, cancellous material, a thermoplastic polymer, ultra-high molecular weight polyethylene, PEEK (polyether-etherketone), stainless steel, titanium, tantalum, nitinol (nickel titanium), PLA (polylactide), PGA, PMMA, or a combination of these materials.

The device 200 can stabilize the stifle joint 10 in a number of ways. The device 200 can function as a mechanical buttress to block the translation of the femur 20 on the tibia 30, thus preventing or reducing instability of the stifle joint 10. In embodiments including a hollow buttress 210 loaded with a biocompatible material, the device 200 can also increase the stability of the stifle joint 10 when the material exits through openings or fenestrations in the buttress 210. The material, such as but not limited to collagen and PMMA microspheres, can induce generation of fibrous tissues into and around intra-articular portions of the device 200, thus stabilizing the joint 10. Further, in some embodiments, the buttress 210 comprises a material having a smooth surface, enhancing the generation of fibrous tissues around the stifle joint 10.

As mentioned above, hollow portions of the device 200 can be filled with a biodegradable matrix. In some aspects, the biodegradable matrix includes a collagen matrix containing PMMA microparticles. The matrix may be excreted through fenestrations in the device 200 into the joint 10. The biodegradable matrix can act as a scaffold for canine fibroblasts to encapsulate the PMMA microparticles, to secrete components of the extracellular matrix, and to ultimately absorb the biodegradable collagen matrix. The biodegradable matrix can invoke the host's inflammatory response to provoke a fibrotic response to the device 200 and stimulate the host to produce collagen and other extracellular components to replace the biodegradable matrix where it is excreted into the subject, thus strengthening the stifle joint 10 further.

In one embodiment, the buttress 210 is a biocompatible material that is completely or partially coated with a collagen and PMMA microsphere coating to induce collagenesis. In another embodiment, the ventral surface 280 of the buttress 210 is porous coated to facilitate incorporation of a collagen PMMA matrix onto the buttress 210. Upon delivery, the device 200 can contact at least a portion of a ligament that is deficient or would benefit from additional support, such as the cranial cruciate ligament or other ligament. As the collagen and PMMA microparticles invoke the animal to produce collagen and extracellular matrix, the strength of the ligament at the site of implantation can increase. In some embodiments, the device 200 is delivered to stabilize the cranial cruciate ligament 40 of the canine stifle joint 10.

It will be understood that other coatings capable of inducing collagenesis can also be used. By coating portions of the device 200 with a material to induce collagenesis, intra-articular portions of the device 200 can eventually create fibrous tissues, which can advantageously remain smooth and preserve most of the articular joint 10.

The device 200 can also stabilize the joint 10 by coating the keel 220 with a material with an affinity for bony ingrowth. In one embodiment, the keel 220 of the device 200 is coated with hydroxyapatite, allowing osseointegration to occur. Further, anchoring the device 200 to the stifle joint 10, or to an area surrounding the stifle joint 10, such as the femur 20 or the tibia 30, can further stabilize the stifle joint 10. As described above, the device 200 can be anchored to the stifle joint 10 by fastening the keel 220 to the femur 20, the tibia 30, or another area surrounding the stifle joint 10. In some implementations, the keel 220 is anchored to the femur 20 or the tibia 30 to provide fixation of the device 200 while osseointegration occurs.

Each or a combination of the aforementioned features can result in increased stability of a canine stifle joint with a deficient cranial cruciate ligament. Advantageously, the devices and methods described herein can minimize the destructive forces that typically occur with TPLO and TTA procedures.

The intra-articular and extra-articular components of the device 200 can be formed in a variety of shapes and sizes to accommodate canine stifle joints of various sizes and shapes. For example, the device 200 can include a small buttress 210 and a small keel 220 for a delivery to a small dog breed such as a dachshund; a mid-size buttress 210 and a mid-size keel 220 for a mid-size dog breed such as a golden retriever; or a large buttress 210 and a large keel 220 for delivery to a large dog breed such as a mastiff.

Embodiments of devices described herein can also include one or more radiopaque markers to identify any change in position after the device is delivered to the stifle joint 10. For example, radiopaque markers may be placed in medial, lateral, anterior, and posterior positions in the device 200 to identify whether the device 200 remains aligned with the stifle joint 10 or has changed position since implantation.

Referring now to the microparticles that can be in or on the buttress 210, microparticles can be microspheres, and/or nanoparticles. As will be understood, microparticles may be small enough to be delivered to a site, but large enough to resist phagocytosis and the lymphatic and blood system from washing away any of the microparticles. As such, microparticles can have a diameter of greater than about 10 µm. In some embodiments, the microparticles can have a diameter between about 20 µm to about 200 µm, a diameter between about 25 µm to about 100 µm, or a diameter between about 20 µm to about 40 µm or between about 30 µm to about 50 µm. The microparticles can also be highly refined to limit any inflammation from smaller particles, and to increase the roundness and smoothness properties of the particles.

The microspheres can comprise an inert, histocompatible material, such as glass, hydroxyapatite, powdered bone, or a polymer. The polymer can be cured and polymerized prior to implantation to reduce toxic or carcinogenic potential of the monomers or cure agents. The inert histocompatible polymer can be an acrylic polymer. The acrylic polymer can be a polymer of methacrylate or one of its esters, such as methyl methacrylate, ethyl methacrylate, n-butyl methacrylate, isobutyl methacrylate, lauryl methacrylate, and 2-ethylhexyl methacrylate or any combination or copolymer thereof. In preferred embodiments, microparticles can comprise polymethylmethacrylate (PMMA). Some embodiments in the form of a gel or paste are described in U.S. Pat. No. 5,344,452, which is incorporated by reference in its entirety.

The microparticles can be suspended in a suspension agent. The suspension agent can be an aqueous or non-aqueous solution. The suspension agent can be of sufficient viscosity to promote the suspension of the microparticles. The suspension agent can be, for example, up to about 0.1%, 0.2%, 0.5%, 1.0%, 2.0%, 5.0%, 10%, 15%, 20%, 30%, 40%, 50%, 60%, 70% and 80% by volume microparticles. The amount of microparticles used is determined in part by other components of the suspension agent, such as the carrier concentration, and the method of implantation.

The suspension agent can also contain a polymer, which can be histocompatible, as a carrier. Such a carrier can be a biodegradable matrix. A biodegradable matrix can comprise a biodegradable polymer. Examples of biodegradable polymers include collagen, albumin, gelatin, chitosan, hyaluronic acid, starch, cellulose, cellulose derivatives (e.g. methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, polysaccharides, fibrinogen, poly(D, L lactide), poly (D, L-lactide-co-glycolide), poly (glycolide), poly(hydroxybutyrate), poly(alkylcarbonate), poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids), and copolymers thereof (see generally, Ilium, L., Davids, S. S. (eds.) "Polymers in Controlled Drug Delivery" Wright, Bristol, 1987; Arshady R., "Preparation of biodegradable microspheres and microcapsules." J. Controlled Release 17:1-22, 1991; Pitt C. G., "The controlled parenteral delivery of polypeptides and proteins." Int. J. Pharm. 59:173-196, 1990; Holland et al, "Polymers for Biodegradable Medical Devices. 1. The Potential of Polyesters as Controlled Macromolecular Release Systems." J. Controlled Release 4:155-180, 1986).

In some implementations, the biodegradable polymer can comprise collagen. Collagen may allow for the separation of the microspheres to allow tissue ingrowth. The collagen can be in many types and forms, or in combinations thereof For example, collagen can be Type I, II or III. Collagen can be native, denatured or cross linked. The various types and forms of collagen are described generally in Methods in Enzymology. (1982) 82:3-217, Pt. A, incorporated by reference in its entirety. For example, collagen can be produced from animal derived tissues such as bovine or porcine hides, avian combs, human tissues such as cadaver skin or human cell cultures or through recombinant methods. In some embodiments, the device 200 includes a collagen fully dissolved or in suspension. The solution can contain up to about 0.1%, 0.2%, 0.5%, 1.0%, 2.0%, 2.5%, 3.0%, 3.5%, 4.0%, 4.5%, 5%, 6%, 7%, 8%, 9%, 10%, 20%, 30%, 40%, 50%, 60%, 70%, or 80% (v/v) collagen content. The amount of collagen content in the solution is in part determined by the resultant viscosity, the percentage of other components such as microparticles and the method of implantation.

An example of a commercially available material that may be used in some embodiments includes ARTEFILL (Artes Medical Inc.). ARTEFILL comprises PMMA microparticles suspended in bovine collagen.

Other examples of commercially available materials that have been used for tissue repair and cosmetic applications include bovine collagen products such as ZYDERM I, ZYDERM II, and ZYPLAST (each produced by Allergan Inc.); bioengineered human collagen products such as COSMODERM I, COSMODERM II, and COSMOPLAST (Allegan Inc.); and porcine collagen products such as EVOLENCE (Ortho-McNeil-Janssen Pharmaceuticals, Inc.). More examples of collagen products include collagen meshes such as INSTAT (Johnson & Johnson), and composite collagen meshes such as ALLODERM (Lifecell Corp.), as well as collagen sponges such as SURGIFOAM (Johnson & Johnson) and TERUDERMIS (Terumo Corp.).

The material in or on the buttress 210 can include additional bioactive agents. In some aspects, the device 200 is filled with collagen containing PMMA microparticles and a bioactive agent. The bioactive agent can be incorporated into porous microparticles, for example. Bioactive agents can include any composition that is able to invoke a biological response in a subject. A biological response can include, for example, responses to promote healing such as a fibrotic response, pain relief, or to prevent infection. Examples of bioactive agents that can induce a fibrotic response include silk, talc, chitosan, polylysine, fibronectin, bleomycin. More examples of bioactive agents include local anesthetics (e.g. lidocaine, bupivacaine, procaine, tetracaine, dibucaine, benzocaine, p-buthylaminobenzoic acid 2-(diethylamino) ethyl ester HCl, mepivacaine, piperocaine, dyclonine, and opioids such as morphine, diamorphine, pethidine, codeine, hydrocodone, and oxycodone), non-steroidal anti-inflammatory drugs (e.g. ketoprofen, auranofin, naproxen, acetaminophen, acetylsalicylic acid, ibuprofen, phenylbutazone, indomethacin, sulindac, diclofenac, paracetamol, and diflunisal, Celecoxib, and Rofecoxib), antibiotics (e.g. clindamycin, minocycline, erythromycin, probenecid, and moxifloxacin), and antineoplastic agents. Antineoplastic agents can have antimicrobial activity at extremely low doses; examples include anthracyclines (e.g. doxorubicin and mitoxantrone), fluoropyrimidines (e.g. 5-FU), folic acid antagonists (e.g. methotrexate), podophylotoxins (e.g. etoposide), camptothecins, hydroxyureas, and platinum complexes (e.g. cisplatin). In one embodiment, the implantable device includes lidocaine. The concentration of lidocaine can be less than about 0.1%, 0.2%, 0.3%, 0.5%, 0.7%, 0.8%, 0.9%, 1%, and 5% by weight.

As used herein "subject" or "host" can refer to an animal that can benefit from the methods and devices described herein. As will be understood by one of skill in the art, "need" is not an absolute term and merely implies that the subject can benefit from the methods and devices described herein. In preferred embodiments, the subject is a dog.

A subject can be identified by various methods, including, for example, by palpation, arthrotomy, x-ray, ultrasound, joint taps, and magnetic resonance imaging. Such methods can indicate stifle instability, and/or injury to the ligaments of the stifle joint.

Various modifications to these examples may be readily apparent to those skilled in the art, and the principles defined herein may be applied to other examples without departing from the spirit or scope of the novel aspects described herein. Thus, the scope of the disclosure is not intended to be limited to the examples shown herein but is to be accorded the widest scope consistent with the principles and novel features disclosed herein. Accordingly, the novel aspects described herein is to be defined solely by the scope of the following claims.

What is claimed is:

1. A device for promoting stability of the stifle joint in a canine subject comprising:
a buttress comprising a single object having an intra-articular surface and an extra-articular surface enclosing a hollow space, wherein the hollow space contains a biodegradable matrix comprising collagen and a plurality of microparticles adapted to be excreted through a plurality of fenestrations in the intra-articular surface of the buttress; and a keel coupled to the extra-articular portion of the buttress; and one or more fasteners configured to attach the device to the stifle joint of the canine subject.

2. The device of claim 1, wherein the buttress is generally cylindrical.

3. The device of claim 1, wherein the intra-articular surface of the buttress comprises one or more tapered portions.

4. The device of claim 1, wherein the fasteners are configured to attach the keel to a tibia of the canine subject.

5. The device of claim 1, wherein the fasteners are configured to attach the keel to a femur of the canine subject.

6. The device of claim 1, wherein an intra-articular portion of the buttress is hollow.

7. The device of claim 1, wherein the buttress contains a port.

8. The device of claim 1, wherein the plurality of microparticles comprise one or more materials selected from poly methacrylate, polymethyl methacrylate, hydroxyapatite, powdered bone, or glass.

9. The device of claim 1, wherein a portion of the buttress is coated with a biodegradable matrix.

10. The device of claim 9, wherein the biodegradable matrix comprises collagen and a plurality of microparticles.

11. The device of claim 1, wherein the device further comprises a bioactive agent.

12. The device of claim 11, wherein the bioactive agent comprises an agent selected from the group consisting of a local anesthetic, non-steroidal anti-inflammatory drug, antibiotic, and antineoplastic agent.

13. The device of claim 1, wherein the device comprises one of a thermoplastic polymer, ultra-high molecular weight polyethylene, stainless steel, titanium, tantalum, nitinol, PMMA, PLA, and PGA.

14. The device of claim 1, wherein the keel is coated with hydroxyapatite.

15. A biocompatible device to prevent instability in the canine stifle joint of a canine subject comprising:

a buttress comprising a single hollow object having an intra-articular surface and an extra-articular surface, wherein the buttress contains a biodegradable matrix comprising collagen and a plurality of microparticles adapted to be excreted through a plurality of fenestrations in the intra-articular surface of the buttress; and a plate that is attachable to the femur or the tibia of the canine subject.

16. The device of claim 15, wherein the buttress is filled with PMMA microspheres and collagen.

17. The device of claim 15, comprising a biocompatible material.

18. The device of claim 17, comprising one of a thermoplastic polymer, ultra-high molecular weight polyethylene, stainless steel, titanium, tantalum, nitinol, PMMA, PLA, and PGA.

19. The device of claim 15, wherein the plate is configured to be anchored to the anterior portion of the tibia such that the plate is screwed in and locked into position.

20. The device of claim 19, wherein the plate is anchored to the tibia with one or more screws.

* * * * *